(12) United States Patent
Huppenthal et al.

(10) Patent No.: US 8,870,059 B1
(45) Date of Patent: *Oct. 28, 2014

(54) LABORATORY SAMPLING MACHINE AND METHODS FOR MAINTAINING CHAIN OF CUSTODY FOR SAMPLES

(76) Inventors: Joe Huppenthal, Flagstaff, AZ (US); Drew Miller, Flagstaff, AZ (US)

( * ) Notice: Subject to any disclaimer, the term of this patent is extended or adjusted under 35 U.S.C. 154(b) by 219 days.

This patent is subject to a terminal disclaimer.

(21) Appl. No.: 13/540,354

(22) Filed: Jul. 2, 2012

Related U.S. Application Data

(63) Continuation-in-part of application No. 12/687,129, filed on Jan. 14, 2010, now Pat. No. 8,297,151, and a continuation-in-part of application No. 12/717,876, filed on Mar. 4, 2010, now Pat. No. 8,235,281, which is a continuation of application No. 12/616,783, filed on Nov. 12, 2009, now abandoned.

(60) Provisional application No. 61/145,521, filed on Jan. 17, 2009, provisional application No. 61/114,251, filed on Nov. 13, 2008.

(51) Int. Cl.
*G06F 17/00* (2006.01)
(52) U.S. Cl.
USPC .......................................................... 235/375

(58) Field of Classification Search
USPC .......................................................... 235/375
See application file for complete search history.

(56) References Cited

U.S. PATENT DOCUMENTS 8,235,281 B1 * 8/2012 Miller et al. ................... 235/375

* cited by examiner

*Primary Examiner* — Christle I Marshall
(74) *Attorney, Agent, or Firm* — Coastal Patent Law Group, P.C.

(57) ABSTRACT

A machine and methods for maintaining chain of custody during a sampling procedure is provided, the machine including a sample handling robot having an operation head and a verification head. The verification head can be one of a barcode reader, OCR scanner, of RFID tag reader. The verification head of the machine is adapted to read a sample container prior to sampling an aliquot of liquid, and transferring the aliquot to a testing vial. Each sample container and corresponding testing vial is read prior to performing an operation, such that a chain of custody is properly recorded. The machine can further comprise a lid-opening and closing device adapted for articulating the lid of one or more standard vial types. Additionally, the machine may comprise a manual vial staging area for non-standard vial types. The machine may be further adapted to prepare diluted testing samples or combined reagent samples.

13 Claims, 4 Drawing Sheets

LABORATORY SAMPLING MACHINE AND METHODS FOR MAINTAINING CHAIN OF CUSTODY FOR SAMPLES

CROSS-REFERENCE TO RELATED APPLICATIONS

This application is a continuation-in-part of U.S. patent application Ser. No. 12/687,129, filed Jan. 14, 2010, which claims benefit of priority to U.S. Provisional Application Ser. No. 61/145,521, filed Jan. 17, 2009; and a continuation-in-part of U.S. Ser. No. 12/717,876, filed Mar. 4, 2010, which is a continuation of U.S. patent application Ser. No. 12/616,783, filed Nov. 12, 2009, which claims benefit of priority to U.S. Provisional Application Ser. No. 61/114,251, filed Nov. 13, 2008;

the entire contents of each of which are hereby incorporated by reference, and hereafter each of these references may be collectively referred to herein as "referenced applications".

FIELD OF THE INVENTION

The present invention relates to a laboratory sampling machine and related methods, and more specifically to a machine and methods for high-throughput sample processing for use in laboratory testing and related applications.

BACKGROUND OF THE INVENTION

Certain problems and limitations in the art of automated laboratory sampling equipment are described in commonly owned U.S. patent application Ser. No. 12/717,876, filed Mar. 4, 2010; commonly owned U.S. patent application Ser. No. 12/687,129, filed Jan. 14, 2010; and commonly owned U.S. patent application Ser. No. 12/616,783, filed Nov. 12, 2009, and published as US 2010/0116876.

In addition, it has been recognized that certain problems currently exist relating to the multitude of available sample vial sizes, such that no single standardized vial is utilized across the board in the medical, substance testing, and related industries. Accordingly, a machine for automated sample processing must be adapted to accept a variety of vial designs, or a manual transfer of the sample to an accepted vial design may be required.

Various embodiments herein seek to address one or more limitations relating to these and other vial design attributes.

SUMMARY OF THE INVENTION

In sum of certain embodiments of the invention, a laboratory sampling machine is provided; the machine is adapted for computer automated processing of various samples thereby minimizing contamination and other concerns while maintaining a detailed chain of custody for samples.

In a general embodiment, a laboratory sampling machine comprises an operation head for aspirating samples and a verification head for reading informational content of a vial. Furthermore, a computer coupled to the machine is adapted to obtain and record various informational data relating to each step of a processed sample for maintaining a chain of custody. The machine is adapted to translate the verification head to a position suitable for reading informational content of a provided vial. Additionally, the machine is adapted to translate the operation head to a position suitable for performing an aspiration of a sample. In this regard, the machine is adapted to read and record on a computer various informational data associated with source and destination vials or containers, as well as other data relating to the chain of custody for each sample such that a record history can be produced as may be desired.

In one embodiment, the operation head and verification head are independently controlled about a vertical axis.

In another embodiment, the operation head and verification head are collectively controlled about a Cartesian plane.

In another embodiment, the laboratory sampling machine comprises a lid opening device at a first station.

In another embodiment, the laboratory sampling machine comprises a multi-lid station, wherein the multi-lid station comprises an automated lid opening device for automated opening and staging of a vial in accordance with one or more standard vial designs, and a manual staging device for non-standard vials.

In another embodiment, the laboratory sampling machine is adapted to aspirate a sample from a provided vial and dispense an aliquot of the sample into one or more destination vials.

In yet another embodiment, the laboratory sampling machine is adapted to dilute or combine one or more reagents with an aliquot of the sample for enhanced sample preparation and processing.

In another aspect of the invention, certain methods are described for processing samples in the laboratory sampling machine described herein.

Other features and benefits of the invention will be hereinafter described.

BRIEF DESCRIPTION OF THE DRAWINGS

These and other attributes of the invention will become more clear upon a thorough study of the following description of the invention, particularly when reviewed in conjunction with the drawings, wherein.

DETAILED DESCRIPTION OF THE INVENTION

Figure 1:
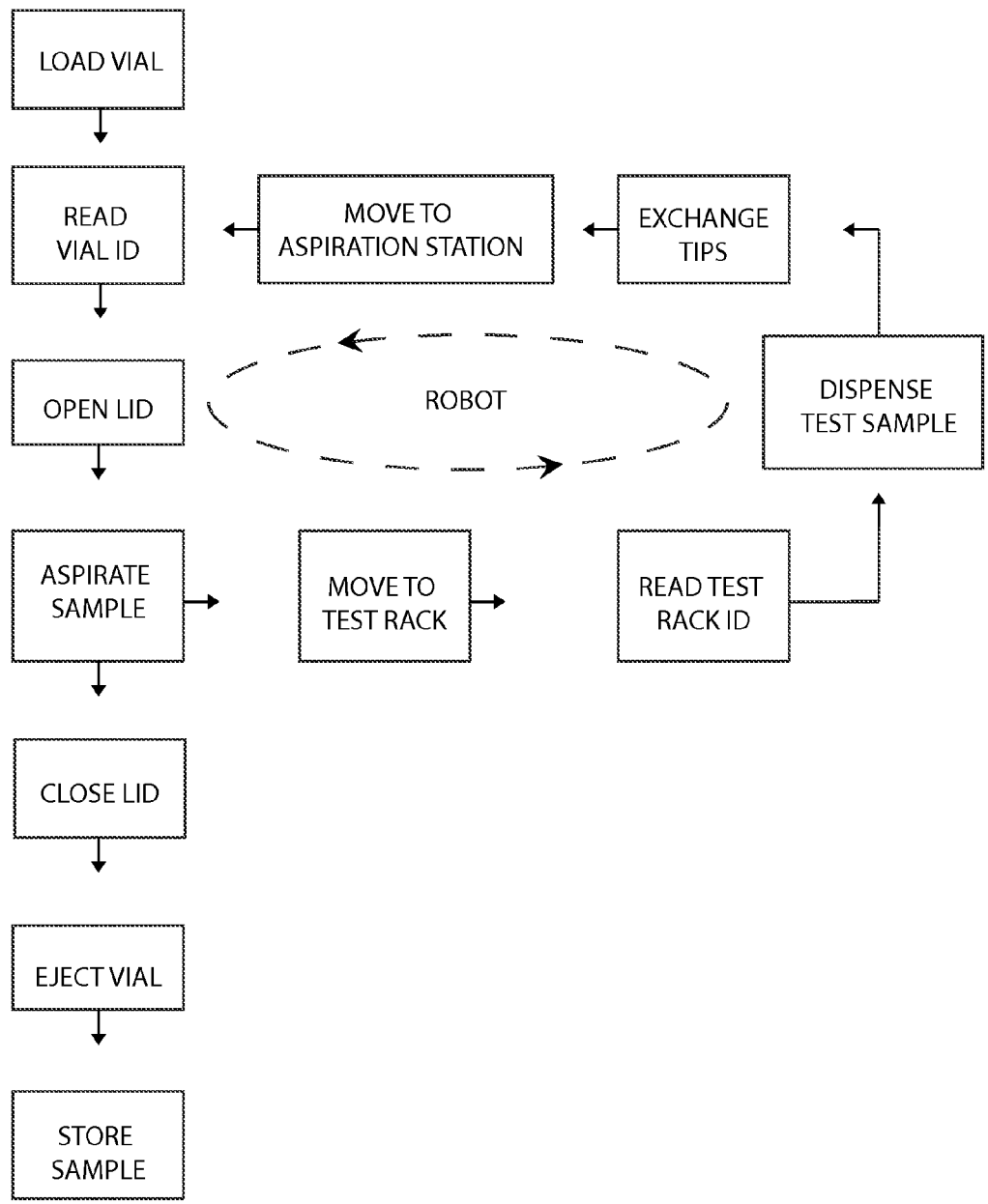
FIG. 1 illustrates a flow chart depicting a series of programmable steps performed by a computerized laboratory sampling machine in accordance with various embodiments of the invention.

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

Certain embodiments will be described below with reference to the drawings wherein illustrative features are denoted by reference numerals.

As detailed above, a comprehensive description of certain features and benefits of an automated laboratory sampling machine is disclosed in commonly owned U.S. patent application Ser. No. 12/717,876, filed Mar. 4, 2010; commonly owned U.S. patent application Ser. No. 12/687,129, filed Jan. 14, 2010; and commonly owned U.S. patent application Ser. No. 12/616,783, filed Nov. 12, 2009, and published as US 2010/0116876.

DEFINITIONS

For purposes of this invention, the term "environmentally controlled chamber" is defined as a chamber surrounding the laboratory sampling machine and adapted for one or more of: humidity control, temperature control, pressure control, light shielding, and RF shielding.

The term "automatic vial opening" is defined as a procedure performed by a lid-opening and closing device, wherein the lid of the vial is automatically opened by the device.

The term "manual vial opening" is defined as a procedure performed by a technician, wherein the lid of the vial is manually opened by the technician.

The term "reagent" is defined as a substance used in a chemical reaction to detect, measure, examine, or produce other substances.

The term "diluent" is defined as a substance, such as water or saline, used to dilute the concentration of a given sample.

The term "sample" is defined as a specimen of solid, gas, fluid, blood or tissue collected for analysis on the assumption that it represents the composition of the whole.

The term "containers" is broadly defined to include vials, receptacle, or other containment vessels adapted to contain samples, reagents, or diluents.

Laboratory Sampling Machine w/Multi-Vial Staging

In furtherance of the embodiments disclosed in the above-referenced commonly owned patent applications, or "referenced applications", it has been further recognized that due to a myriad of available vial designs, including a multitude of various shapes, sizes, volumes, and other design aspects, a lid-opening and closing device engineered for opening lids of one or few specific vial types can present some limitation with respect to efficiency and productivity of automated sample processing when utilizing an automated laboratory sampling machine to process samples. For example, where a sample is provided in a standard vial size for which the lid opening device is adapted to function the automated process is efficiently executed. However, where such a sample is provided in a non-standard vial size, and the lid opening device is not adapted to open the lid of the particular vial, and one or more compensating tasks must be contemplated, such as transferring the sample to an accepted or standard vial size, of manipulating the laboratory sampling machine to aspirate the sample from a non-standard vial. In either course of action, human error can be introduced into the system, or added notes or details may be required for entry into the computerized log for maintaining a proper chain of custody.

Accordingly, a laboratory sampling machine is disclosed which overcomes these and other related limitations.

In a general embodiment, the laboratory sampling machine comprises an operation platform having multiple stations. The multiple stations may comprise a first station for lid-opening and sample-staging; a second station for transferring an aliquot of sample acquired from the sample staging station into a testing vial; a third station for purging and dispensing waste; and a fourth station for acquiring a sterile tip such as a pipette tip.

In certain embodiments, the platform may further comprise a diluent station for distributing one or more diluent solutions for diluting a sample to a desired concentration.

In certain other embodiments, the platform may further comprise a reagent station for distributing one or more reagent solutions for combining reagents with a sample to form a desired solution.

The diluent and reagent stations are not illustrated since one having skill in the art would be able to make and use such platform stations in view of the above-referenced applications and common industry practices.

The laboratory sampling machine further comprises at least one sample handling robot. The sample handling robot further comprises an operation head for aspirating samples and a verification head for reading informational content of a vial. The robot is adapted to translate the verification head to a position suitable for reading informational content of a provided vial. Additionally, the robot is adapted to translate the operation head to a position suitable for performing an aspiration of a sample.

In one embodiment, the robot is adapted to independently translate each of the operation and verification heads about a vertical axis. In this regard, the operation head can be translated about a vertical axis to a position adjacent to a sample for enabling an aspiration thereof. Additionally, the verification head can be vertically translated to a position adjacent to an identification member containing informational data relating to a particular vial or container, such as, for example, a barcode, alphanumeric (for use with OCD scanning) or RFID tag.

In various embodiments, the robot is further adapted to translate about a Cartesian plane for accessing the multiple stations about the platform.

Of importance to certain embodiments herein, the first lid-opening and sample-staging station may comprise a standard vial staging area with an automated lid-opening and closing device, and a non-standard vial staging area requiring manual lid removal and open vial staging. In this regard, the lid opening device of the standard vial staging area can be adapted to open and close the lid of one or more standard vial types, whereas the non-standard vial staging area is adapted to accept a sample having a lid removed by a technician. For purposes herein, a laboratory sampling machine having a first lid-opening and sample-staging station with both a standard vial staging area having an automated lid-opening and closing device, and a non-standard vial staging area for manual lid removal can be referred to as a laboratory sampling machine adapted for "multi-vial staging".

It should be noted that multi-vial staging can be accomplished with: (i) a standard vial station with a single lid-opening and closing device adapted to open the lid of a single vial type (standard vial/single lid-actuator), and a manual staging area adapted to introduce other non-standard vial types; (ii) a standard vial station with a multi-lid-opening and closing device adapted to open a lid of two or more distinct vial types (multiple standard vials/single lid-actuator), and a manual staging area adapted to introduce other non-standard vial types; or (iii) a plurality of lid-opening and closing devices (single or multiple standard vials/multiple lid-actuators), and a manual staging area for non-standard vial types.

Where a multi-vial staging station is provided with the laboratory sampling machine, a mechanism for determining which of the multiple staging areas should be aspirated or identified using the operation and verification heads, respectively, can be provided. Such a mechanism may comprise a mass sensor adapted to sense mass of an inserted vial, such as any mass sensor that is commonly available and well recognized in the art; an optical sensor such as an infrared, laser, or other optical sensor for determining the presence of a vial in one of the multiple staging areas of first station; or any other detector known in the art; or alternatively a user-provided command for initiating a read and operation at one of the staging areas of the first station. The purpose of the mechanism is to recognize an instruction for translating the robot to a particular staging area for initiating an identification read and an operation head action, and such mechanism can be accomplished by several known methods, and is not necessarily limited to the forgoing examples.

In this regard, the automated laboratory sampling machine is adapted for multi-vial staging at a first lid-opening and vial staging station of the operation platform. Depending on the circumstances of the introduced sample, an appropriate lid-opening action may be executed and a read and aspiration initiated at an appropriate staging area. Subsequent to the multi-vial staging and initial sample aspiration, the laboratory sampling machine may perform one or more pre-programmed operations in accordance with a sample processing sequence.

Figure 4:
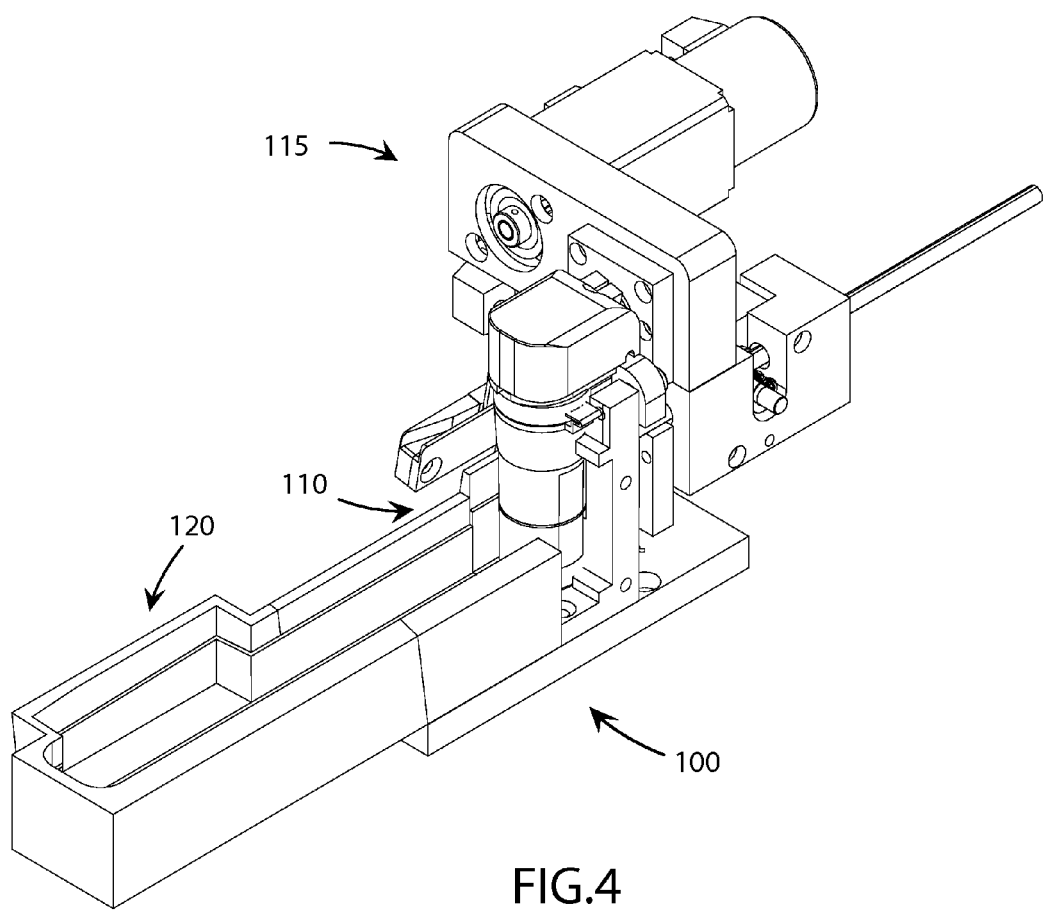
FIG. 4 illustrates a multi-vial lid opening station in accordance with an embodiment of the invention.

For purposes of illustration, FIG. 4 depicts an example of a multi-vial staging station in accordance with an embodiment of the invention. The multi-vial staging station 100 is generally positioned about the operational platform of the laboratory sampling machine at an area designated for providing samples. The multi-vial staging station comprises a standard vial staging area 110 having an automated lid-opening and closing device 115 adapted to open and close a vial lid of a standard vial, and a non-standard vial staging area 120. When providing a non-standard vial, being a vial having a size or shape that is not accepted by the lid opening device, the non-standard vial can be manually opened and placed in the non-standard vial staging are. In the case of a standard vial, the automated lid opening device 115 is positioned adjacent to the standard vial staging area 110 and adapted to open and close a lid of a standard vial placed therein.

Sample Dilution and Reagent Preparation within an Automated Laboratory Sampling Machine In certain embodiments of the invention, the laboratory sampling machine may further be adapted for one or more of: sample dilution, and reagent combination.

As described above, the operation platform may comprise a diluent station or a reagent station. Although distinct stations being located with distinct coordinates within the Cartesian plane of the robot translational space, each of the dilution and reagent stations is similar in that they independently may comprise one or more containers filled with one of a diluent or a reagent solution. Additionally, the robot is adapted to translate about the Cartesian plane to a position near the respective diluent or reagent container, and translate the operation head to a position for aspirating an aliquot of the respective diluent or reagent solution. Additionally, it may be desirable to further translate the verification head to read informational data associated with the diluent or reagent container, in which case the verification head is generally translated and utilized prior to the operation head and associated aspiration, however, the verification may optionally be performed subsequent to the aspiration and no limitation is predisposed.

Now turning to an embodiment as illustrated in FIG. 01, the laboratory sampling machine can be adapted to perform a first operation sequence as illustrated. The first operation will be referred to as "mode 1", which may be selectable from a computerized menu coupled to the laboratory sampling machine. In accordance with mode 1, a vial is loaded into the first station of the operation platform. The robot translates to the first station and a verification head of the robot further translates to a position adjacent to an identification member of a vial, and executes a read of the vial identification member. The identification member may include a barcode, RFID, or other identification means as would be available in the art. The lid is opened, preferably using a lid-opening and closing device, and an operation head translates to a position for aspirating an amount of sample contained in the vial. Subsequent to the sample aspiration from the provided source vial, the robot is programmed to move the operation hand verification heads toward a test rack where a number of testing vials are provided, and the lid of the source vial is closed, preferably using the lid-opening and closing device. At the first station, the vial is ejected, and subsequently, the vial is stored for future use. Meanwhile, the robot was translated to the test rack, the verification head is translated to a position suitable for reading a destination ID (such as a test rack ID or a testing vial ID), and an aliquot of the sample is dispensed into a testing vial. The robot may now translate to a waste station to purge any remaining sample and eject a tip, translate to a tip station to acquire a sterile tip, and return to the aspiration station to begin aspiration of a subsequent sample. This process is repeated as many times as necessary to process all samples in a sample batch. When complete, a test rack may comprise a number of testing vials each containing an amount of sample and being prepared for subsequent processing in a testing machine, for example a chromatography or other analytical testing machine. Moreover, each testing vial and sample contained therein will be associated with data logged in the computer as the chain of custody for all sample aliquots distributed to the testing vials was continuously tracked using the verification head reader.

It should be noted that the embodiment of "mode 1" utilizes two active loops including a robot loop, which translates between the sample staging station, the testing rack station, the waste station, and the tip station, and a staging loop, which includes receiving a vial, opening of the vial lid, reading the vial, aspirating a sample from the vial, closing the lid, and ejecting the vial for storage. Additionally, the testing rack station, waste station, and tip station can be deemed as passive stations since the robot is the only active component working at these stations.

Figure 2:
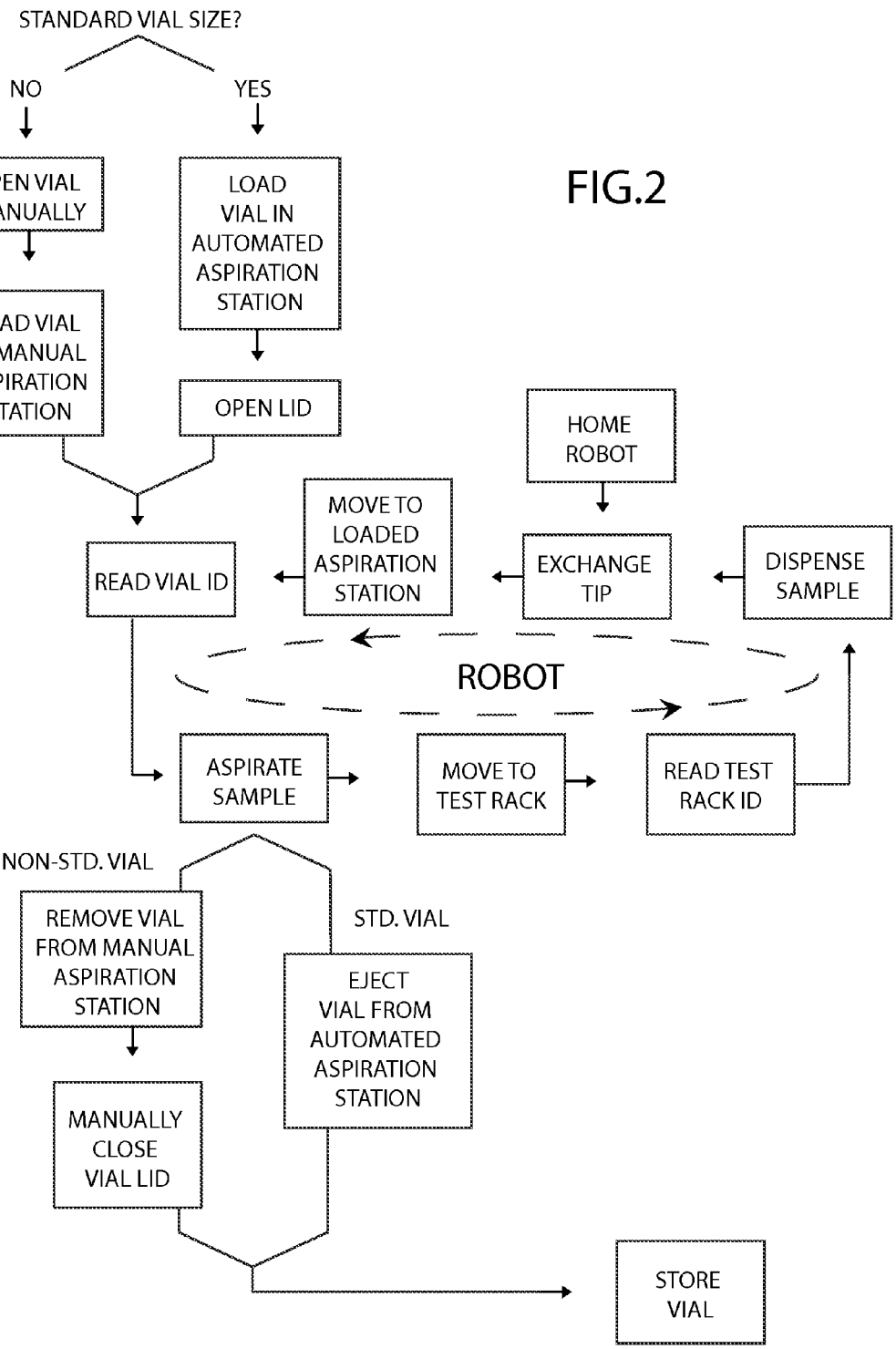
FIG. 2 illustrates a flow chart depicting a series of programmable steps performed by a computerized laboratory sampling machine in accordance with various embodiments of the invention, wherein the machine comprises a multi-vial lid opening station adapted for automated lid opening of one or more standard vial designs and manual lid opening of non-standard vial designs.

In another embodiment, as illustrated in FIG. 2, a second operation sequence for which a laboratory sampling machine may be adapted to perform. The second operation will be referred to as "mode 2", which, like mode 1, may be selectable from a computerized menu coupled to the laboratory sampling machine. In accordance with mode 2, a multi-vial staging station is provided according to various embodiments herein. The multi-vial staging station is disposed at the first station of the operation platform and comprises at least one automated staging area having a lid-opening and closing device, and at least one manual vial staging area. In this regard, the user places a vial in the first station, with the vial in the automated staging area if the vial is a standard size, or alternatively with the vial in the manual staging area if the vial is of a non-standard size. Prior to placing in the manual staging area, the lid of the vial is removed manually. If placed in the automated station, the lid-opening and closing device removes the lid prior to aspiration. The first station may further comprise a means for detecting the presence of a vial in one or more of the automated staging area or the manual staging area. Alternatively, a user may prompt the computerized control by selecting the location of the vial prior to aspiration of a sample aliquot therefrom. Accordingly, by any means prompted, the robot of the laboratory sampling machine is adapted to translate to a position suitable for reading a vial identification member for the given sample.

Once the provided vial is identified by the verification head of the robot, the operation head may aspirate a sample, move to the test rack, read the test rack ID (or testing vial ID), and dispense an aliquot of sample into the testing rack in a similar sequence as described in mode 1, above. After dispensing the sample aliquot, the robot may purge and eject the used tip at the waste station, and translate to the tip station for acquiring a new tip. The robot may be homed to a rest position in between sample processing. When ready, the robot is again translated to the first station at one of the staging areas (depending on whether the vial is of a standard size), and the robot loop is repeated as necessary to process all samples of a sample batch. Taking a step back, after the robot has sampled an amount from the provided vial in the first station, and prior to dispensing than aliquot of the sample into a testing vial, the first station may conclude by automatically closing the vial lid and ejecting from the automated staging area (in the case of the standard vial), or the non-standard vial may be manually removed and the lid manually replaced to close the vial. Subsequent to closing the vial lid and removing from the first staging area, the sample may be stored.

Figure 3:
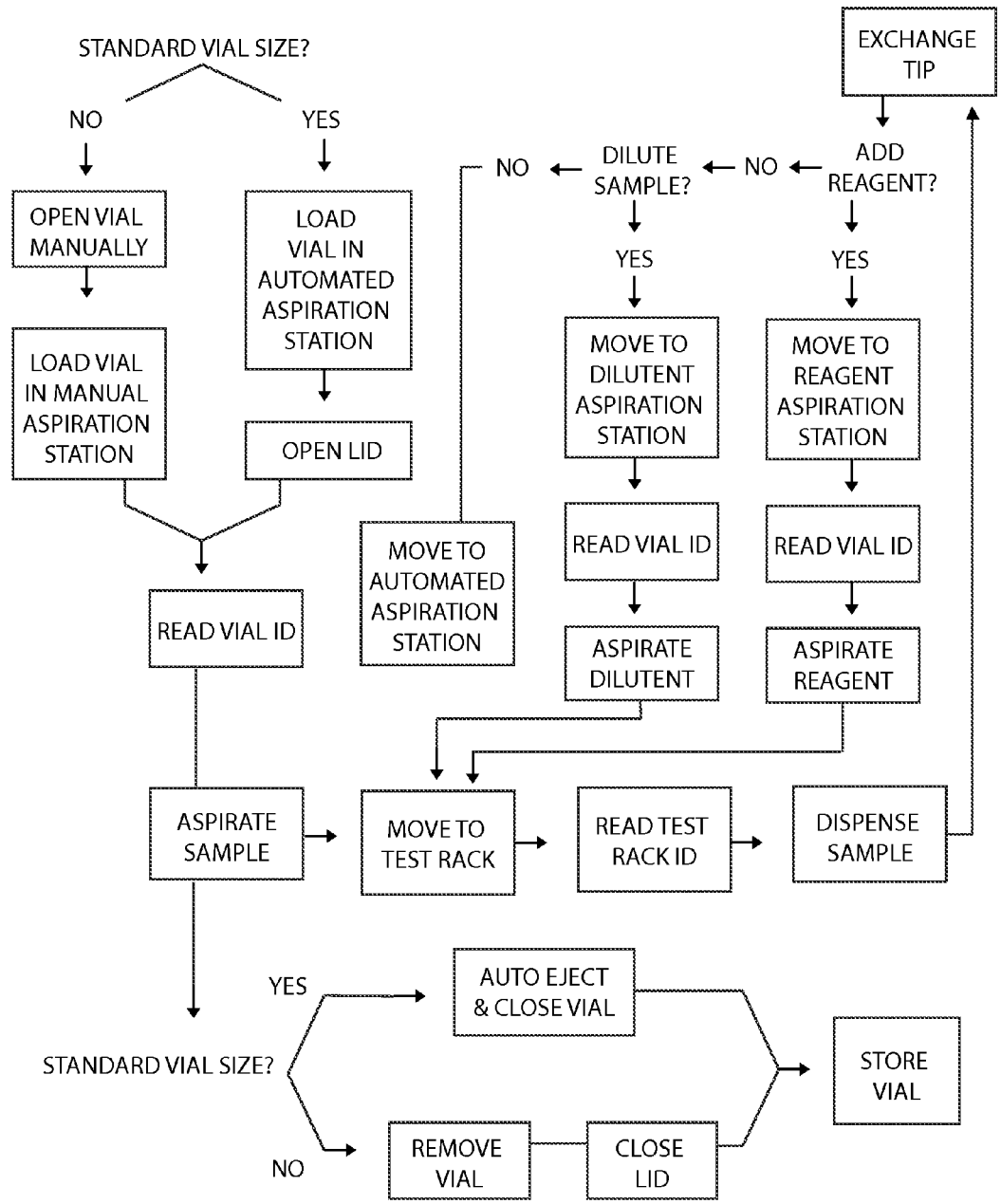
FIG. 3 illustrates a flow chart depicting a series of programmable steps performed by a computerized laboratory sampling machine in accordance with various embodiments of the invention, wherein the machine is further adapted for one or more of sample dilution and reagent combination within an automated and controlled environment.

In yet another embodiment, as illustrated in FIG. 3, a laboratory sampling machine may be adapted to perform a sequence as illustrated, hereinafter referred to as "mode 3". As with modes 1 and 2, mode 3 may be selectable from a computerized menu. A lid-opening and closing station may be provided in accordance with the requirements of a given sample batch, again depending on whether standard size vials are provided. The lid-opening and closing device may therefor comprise multi-vial staging as described above, with at least one automated lid-opening and closing device, and a manual vial staging area. Mode 3 is generally selected where the sample processing sequence requires one or more of sample dilution, and/or reagent combination.

Mode 3 is generally similar to mode 2, wherein mode 3 provides an automated lid-opening and closing function for standard size vials, and a manual vial staging area for non-standard vials. Subsequent to reading the vial ID and aspirating a sample from the provided vial at the first station, the robot may dispense an amount of the sample into one or more destination vials. Additionally, the robot can translate as necessary about the operation platform to exchange tips, aspirate a reagent for combining with the sample aliquot in the destination vial, or aspirate a diluent for diluting the sample in a destination vial. At each station, the verification head is translated and a read is performed against an identification member. Additionally, prior to aspirating any of: a sample, a reagent, or a diluent, the tip is exchanged and the operation head is purged at the waste station. If no reagent or diluent is required, the robot functions in a similar sequence as described in mode 2, above. However, where various diluted samples are required, the laboratory sampling machine is adapted to combine proportions of diluent required to yield the specified products for testing. Similarly, where combined reagent solutions are desired, the laboratory sampling machine is adapted to combine the necessary reagents to yield the desired samples. Subsequent to dispensing the needed aliquot(s) of the sample from the provided vial at the first station, the lid of the provided vial may be closed by way of an automated close and eject performed by the lid-opening and closing device, or by manual close and removal of the vial from the first station staging area. In this regard, the desired solutions and testing samples can be automatically prepared by a robot, with a recorded chain of custody, and in many embodiments with minimized human involvement (minimized human-introduced error) by utilizing an automated lid-opening and closing device.

Utilizing mode 3, multiple diluted samples and/or reagent compositions may be prepared by the laboratory sampling machine. In this regard, testing may yield results illustrating a spectrum of data for multi-dimensional analysis.

In one embodiment, the laboratory sampling machine may be coupled to a computer which is adapted to comprise a computerized menu that is pre-programmed to perform an operation sequence selected from at least one of: mode 1, mode 2, and mode 3, each as described above. Alternatively, the machine may be programmed with a single operation sequence, wherein the sequence is any of mode 1, mode 2, or mode 3.

In certain embodiments, the lid-opening and closing device may be attached to a sub-platform, wherein the sub-platform may be removably attached to the first station of the operation platform. In this regard, various lid-opening and closing devices may be interchangeably configured for use with the laboratory sampling machine depending on user requirements.

ILLUSTRATIVE EXAMPLES

In order to further describe various features and benefits of the invention, certain examples are hereinafter described.

Example 1

Two Samples w/One Test for Each Sample

In a first example, a first sample is obtained from a first patient, and a second sample is obtained from a second patient; the first sample is provided in a first vial of standard size, and the second sample is provided in a second vial of non-standard size. Only one test must be performed using a first analytical instrument, thus only one testing vial per sample should be prepared.

A technician equipped with the laboratory sampling machine as described herein attaches a multi-vial staging station on the machine and selects "mode 2" from a computerized menu.

The technician places the first vial containing the first sample in the automated lid-opening and closing device of the first station of the machine, and the technician instructs the machine that a standard size vial is loaded in the standard vial staging area of the first station. (alternatively, the machine can be adapted to recognize the inserted standard vial, as is described above)

The automated lid-opening and closing device opens the lid of the first vial, the robot translates to the first station, the verification head is positioned to perform a read of the first vial, the data obtained from the verification head is recorded in the computer, and the verification head is returned if it was translated. The operation head is translated to a position for aspirating the first sample of the first vial, an aspiration is performed, and the operation head may retract to a return position before the robot is translated to a test rack.

An aliquot of pre-programmed volume is dispensed into a first testing vial positioned in the test rack after the verification head records the location and associated data of the first testing vial. The robot then translates to the waste station where a purge and tip eject is completed. The robot then translates to the tip station to acquire a new tip.

While the aliquot is being dispensed and the tips exchanged, the automated lid-opening and closing device closes the lid of the first vial and ejects the first vial for removal by the technician.

The second vial is of non-standard size, and thus the technician opens the lid (if any) manually, and inserts the non-standard vial into the manual staging area of the first station.

The robot with a new tip is translated to the first station and the verification head reads and records data associated with an identification member of the second vial. If no data is found, the machine may prompt the technician to enter data or retry the verification read. Once data is acquired from the second sample, the operation head of the robot is positioned for aspiration of the sample, and an aspiration is commenced.

After the aspiration of the second sample, the robot is translated to the test rack where verification is performed at the next sequential testing vial, data is recorded. An aliquot of pre-determined volume is then dispensed into the second testing vial at the testing rack, and the robot is translated to the waste station to purge and eject the used tip prior to obtaining a new tip and returning to a home position.

Meanwhile, the technician may be prompted to remove the non-standard vial, manually close the lid (if any), and store the second vial.

Thus, two testing vials are prepared by the laboratory sampling machine, each containing one of sample 1 or sample 2, and a chain of custody is recorded at each step of the sample preparation sequence. Furthermore, the testing vials are ready for testing in the first analytical instrument.

Example 2

Two Samples w/Two Tests for Each Sample

In a second example, a first sample is obtained from a first patient, and a second sample is obtained from a second patient; the first sample is provided in a first vial of standard size, and the second sample is provided in a second vial of non-standard size. This example is similar to Example 1, except that two tests must be performed for each sample (two tests per patient) using a first and a second analytical instrument, thus two testing vials per sample should be prepared.

A technician equipped with the laboratory sampling machine as described herein attaches a multi-vial staging station on the machine and selects "mode 2" from a computerized menu.

The technician places the first vial containing the first sample in the automated lid-opening and closing device of the first station of the machine, and the technician instructs the machine that a standard size vial is loaded in the standard vial staging area of the first station. (alternatively, the machine can be adapted to recognize the inserted standard vial, as is described above)

The automated lid-opening and closing device opens the lid of the first vial, the robot translates to the first station, the verification head is positioned to perform a read of the first vial, the data obtained from the verification head is recorded in the computer, and the verification head is returned if it was translated. The operation head is translated to a position for aspirating the first sample of the first vial, an aspiration is performed, and the operation head may retract to a return position before the robot is translated to a test rack.

An aliquot of pre-programmed volume is dispensed into a first testing vial positioned in the test rack after the verification head records the location and associated data of the first testing vial. If the aspiration of the first sample contained sufficient volume, a second dispensing is performed at a second testing vial after a verification read of the second testing vial. If the first aspiration of the first sample lacked sufficient sample volume for dispensing in a second testing vial, or if the user-selected parameters require an independent aspiration of the first sample into the second testing vial, the robot is prompted to purge and exchange tips and translate back to the first station to obtain a second aspiration of the first sample prior to returning to the second testing sample of the test rack for dispensing an aliquot therein. The robot then translates to the waste station where a purge and tip eject is completed. The robot then translates to the tip station to acquire a new tip.

While the aliquot is being dispensed and the tips exchanged, the automated lid-opening and closing device closes the lid of the first vial and ejects the first vial for removal by the technician.

The second vial is of non-standard size, and thus the technician opens the lid (if any) manually, and inserts the non-standard vial into the manual staging area of the first station.

The robot with a new tip is translated to the first station and the verification head reads and records data associated with an identification member of the second vial. If no data is found, the machine may prompt the technician to enter data or retry the verification read. Once data is acquired from the second sample, the operation head of the robot is positioned for aspiration of the second sample, and an aspiration is commenced.

After the aspiration of the second sample, the robot is translated to the test rack where verification is performed at the next sequential testing vial, in this case the third testing vial, and data is recorded. An aliquot of pre-determined volume is then dispensed into the third testing vial at the testing rack, and the robot is translated to the waste station to purge and eject the used tip prior to obtaining a new tip and returning to a home position. Similar to above, two testing vials are required for each sample, thus if sufficient volume was obtained in the first aspiration of the second sample at the first station, the robot may immediately dispense a proper aliquot of the second sample into a fourth testing vial. However, if the first aspiration of the second sample did not contain sufficient volume, or if an independent aspiration is requested by the technician, the robot may return to the first station to obtain a second aspiration of the second sample prior to dispensing an aliquot into the fourth testing vial of the test rack.

Meanwhile, the technician may be prompted to remove the non-standard vial, manually close the lid (if any), and store the second vial.

Thus, four testing vials are prepared by the laboratory sampling machine, two each containing one of sample 1 or sample 2, and a chain of custody is recorded at each step of the sample preparation sequence. Furthermore, the testing vials are ready for testing in the first and second analytical instruments.

Example 3

Two Samples w/Three or More Tests for Each Sample

In a third example, the description of "Example 2" can be extrapolated such that three or more testing vials and aliquots therein are prepared from the two samples of patient one and patient two. At the operators preference, the robot may withdraw at least three aliquots worth of sample volume when aspirating each sample, followed by dispensing a single aliquot of the aspirated sample into three testing vials. Alternatively, the sample handling robot may return to the first station to acquire an independent sample aspiration for dispensing into each testing vial. The process is repeated in accordance with "mode 2" as illustrated in FIG. 2 and the associated descriptions.

Example 4

One Sample w/Two Testing Vials Containing Diluted Variants

In a fourth example, a first sample is obtained from a first patient; the first sample is provided in a first vial of standard size. This example requires two testing vials, each containing a diluted variant of the first sample; i.e. 50%, and 25% in saline solution.

A technician equipped with the laboratory sampling machine as described herein attaches a multi-vial staging station on the machine and selects "mode 3" from a computerized menu.

The first vial containing the first sample is inserted into the automated staging area for standard vials which comprises an automated lid-opening and closing device. The lid of the first vial is opened, the robot is translated to the first station and a verification is performed about the first vial. Subsequently, an operation head is translated and an aspiration of the first sample is performed at the first vial.

Because the computer was instructed to prepare one 50% and one 25% diluted variants in testing vials, the volume of the aspirated sample was pre-programmed or pre-calculated. Similar to the above examples, the two testing vials can be prepared using a single sample aspiration from the first station, or each testing vial may be derived from an independent sample aspiration depending on the user parameters that are selected. We will assume for this example that a single sample aspiration is acceptable.

After aspirating the first sample from the first vial at the first station, the robot translates to the test rack and the automated lid-opening and closing device closes the first vial lid prior to ejecting the first vial.

At the test rack, verification is performed about the first testing vial, and two volumetric parts of sample are dispensed into the first testing vial, the robot moves to the second testing vial and performs a verification about the second testing vial prior to dispensing one part of sample into the second testing vial. The robot is translated to a waste station, purged, and the tip is ejected, a new tip is acquired, and the robot translates to the first diluent station. At the first diluent station, a verification read is performed, and the operation head of the robot aspirates a volume of diluent. The robot then translates back to the test rack and performs a read at the first testing vial prior to dispensing two parts of diluent. The robot then translates to the second testing vial, performs a verification read, and dispenses three parts of diluent. The result is a 50% diluted sample in the first testing vial and a 25% diluted sample in the second testing vial, with human error minimized and chain of custody for each sample being maintained.

Example 5

One Sample w/Two Testing Vials Containing Reagent Variants

In a fifth example, a first reagent is provided at a first reagent station, and a second reagent is provided at a second reagent station.

In this example, the machine is configured using "mode 3" in a manner similar to Example 4. However, instead of aspirating diluent in desired proportions, the robot is translated to the first reagent station to aspirate a first reagent into one of the two testing vials, and then translated to the second reagent station to aspirate a second reagent into another of the two testing vials. The robot follows the sequence illustrated in FIG. 3 (mode 3). Tips are exchanged and verifications are performed at each station such that a chain of custody is properly recorded.

It should be noted that the above examples are provided for illustrative purposes only. Tips may be changed as desired prior to aspirating each reagent, diluent, or sample. A verification is performed with identification members being read at each aspiration and dispense function. Due to the volume limitation of various tips, multiple sample aspirations may be used to dispense sample to a desired number of testing vials. Various combinations of sample volume, reagent, diluent, and number of testing vials can be independently configured based on end user requirements.

The above examples are set forth for illustrative purposes and are not intended to limit the spirit and scope of the invention. One having skill in the art will recognize that deviations from the aforementioned examples can be created which substantially perform the same tasks and obtain similar results.

What is claimed is:

1. In a sample preparation machine coupled to a computerized control, a method for sample preparation and maintaining chain of custody throughout a processing sequence, the method comprising:

introducing a sample vial into a first station of an operation platform, the first station comprising a standard vial staging area having an automated lid-opening and closing device adapted to open and close a vial lid of a standard vial, and a non-standard vial staging area;

opening the vial lid of the sample vial;

translating a robot to a tip station and acquiring a sterile tip, the robot comprising an operation head adapted to aspirate one or more samples, reagents, or diluents about one or more containers, and a verification head adapted to perform a data acquisition read about one or more identification members, the sterile tip being affixed to the operation head;

translating the robot to one of the standard vial staging area or the non-standard vial staging area where the sample vial is located;

translating the verification head to a position suitable for reading a first identification member positioned on the sample vial;

recording data associated with the first identification member in memory coupled to the computerized control, and retracting the verification head;

translating the operation head to a position sufficient to perform an aspiration about the sample contained in the sample vial;

aspirating a volume from the sample and retracting the operation head;

translating the robot to a second station of the operation platform comprising a test rack and one or more testing vials disposed therein;

translating the verification head to a position suitable for reading a second identification member positioned on a first testing vial contained within the test rack;

recording data associated with the second identification member in said memory coupled to the computerized control and retracting the verification head;

translating the operation head to a position sufficient to dispense a volume of the sample into the first testing vial;

dispensing a volume of the sample and retracting the operation head;

translating the robot to a third station comprising a waste receptacle, purging residual sample and ejecting the tip;

closing the vial lid of the sample vial; and ejecting the sample vial.

2. The method of claim 1, wherein said opening the vial lid of the sample vial is performed by said automated lid opening and closing device of said standard vial staging area.

3. The method of claim 1, wherein said opening the vial lid of the sample vial is performed by a technician and the sample vial is subsequently placed in the non-standard vial staging area.

4. The method of claim 1, wherein said test rack comprises two or more testing vials.

5. The method of claim 1 repeated for a plurality of samples each contained in a distinct sample vial.

6. The method of claim 1, wherein said sample preparation machine comprises an environmentally controlled chamber.

7. The method of claim 1, further comprising:

introducing at least one reagent container having a third identification member positioned thereon at a reagent station, the reagent station being disposed about said operation platform;

translating the robot to said reagent station;

translating the verification head to a position suitable for reading the third identification member of the reagent container;

recording data associated with the third identification member in said memory coupled to the computerized control, and retracting the verification head;

translating the operation head to a position sufficient to perform an aspiration about a reagent contained in the reagent container;

aspirating a volume of reagent from the reagent container and retracting the operation head;

translating the robot to the second station of the operation platform;

translating the verification head to a position suitable for reading the second identification member positioned on the first testing vial;

recording data associated with the second identification member in said memory coupled to the computerized control and retracting the verification head;

translating the operation head to a position sufficient to dispense a volume of the reagent into the first testing vial;

dispensing a volume of the reagent and retracting the operation head;

translating the robot to a third station comprising a waste receptacle, purging residual reagent and ejecting the tip.

8. The method of claim 1, further comprising:

introducing at least one diluent container having a fourth identification member positioned thereon at a diluent station, the diluent station being disposed about said operation platform;

translating the robot to said diluent station;

translating the verification head to a position suitable for reading the fourth identification member of the diluent container;

recording data associated with the fourth identification member in said memory coupled to the computerized control, and retracting the verification head;

translating the operation head to a position sufficient to perform an aspiration about a diluent contained in the reagent container;

aspirating a volume of diluent from the diluent container and retracting the operation head;

translating the robot to the second station of the operation platform;

translating the verification head to a position suitable for reading the second identification member positioned on the first testing vial;

recording data associated with the second identification member in said memory coupled to the computerized control and retracting the verification head;

translating the operation head to a position sufficient to dispense a volume of the diluent into the first testing vial;

dispensing a volume of the diluent and retracting the operation head;

translating the robot to a third station comprising a waste receptacle, purging residual reagent and ejecting the tip.

9. An automated sample preparation machine, comprising:

an operation platform comprising multiple stations and a robot adapted to translate about a Cartesian plane to a position adjacent to each of said multiple stations;

a first station comprising: a standard vial staging area having an automated lid-opening and closing device adapted to open and close a standard vial lid, and a non-standard vial staging area;

said robot comprising:

an operation head adapted to aspirate one or more samples, reagents, or diluents about one or more containers; and a verification head adapted to perform a data acquisition read about one or more identification members;

a second station comprising a test rack, the test rack further comprising a plurality of testing vials;

a waste station; and a tip station.

10. The automated sample preparation machine of claim 9, further comprising a reagent station.

11. The automated sample preparation machine of claim 9, further comprising a diluent station.

12. The automated sample preparation machine of claim 9, further comprising a sensor for determining whether a vial is placed within said standard vial staging area or within said non-standard vial staging area.

13. The automated sample preparation machine of claim of claim 12, wherein said sensor is one of: a mass sensor, an optical sensor, a laser, or an infrared sensor.

* * * * *